(12) United States Patent
Itagaki et al.

(10) Patent No.: US 6,268,525 B1
(45) Date of Patent: Jul. 31, 2001

(54) PROCESS FOR PRODUCING OPTICALLY ACTIVE CHRYSANTHEMIC ACID

(75) Inventors: Makoto Itagaki, Takatsuki; Goufu Suzukamo, Suita; Kazuaki Sasaki, Misawa; Kunihiko Fujita, Nara, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/238,503

(22) Filed: Jan. 27, 1999

(30) Foreign Application Priority Data

Jan. 29, 1999 (JP) .................................................. 10-016787

(51) Int. Cl.⁷ .................................................. C07B 55/00
(52) U.S. Cl. .......................... 562/401; 560/124; 562/506
(58) Field of Search ..................... 562/401, 506; 560/124

(56) References Cited

U.S. PATENT DOCUMENTS

| 3,646,118 | 2/1972 | Goffinet et al. | 260/514 |
|---|---|---|---|
| 3,739,019 | 6/1973 | Ueda et al. | 260/514 |
| 3,842,125 | 10/1974 | Horiuchi et al. | 260/514 |
| 3,879,451 | 4/1975 | Yoshioka et al. | 260/514 |
| 4,659,864 | 4/1987 | Suzukamo et al. | 560/124 |
| 5,298,660 | 3/1994 | Yoneyoshi et al. | 564/302 |

FOREIGN PATENT DOCUMENTS

| 0 508 307 A2 | 10/1992 | (EP) . |
|---|---|---|
| 49-109344 | 10/1974 | (JP) . |
| 50-151842 | 12/1975 | (JP) . |
| 03074374 | 3/1991 | (JP) . |
| 3-74347 | 3/1991 | (JP) . |

OTHER PUBLICATIONS

Derwent English language abstract of JP 03–074347 A published Mar. 28, 1991.
Derwent English lanaguage abstract of JP 52–034617 B published Sep. 5, 1977.

T. Aratani, "Catalytic asymmetric snythesis of cyclopropane–carboxylic acids: an application of chiral copper carbenoid reaction", *Pure & Appl. Chem.*, vol. 57, No. 12, 1985, pp. 1839–1844.

Richard E. Lwenthal et al., "Symmetric Copper–Catalyzed Cyclopropanation of Trisubstituted and Unsymmetrical cis–1,2–Disubstituted Olefins: Modified Bis–Oxazoline Ligands", *Tetrahedron Letters*, vol. 32, No. 50, 1991, pp. 7373–7376.

Shuji Kanemasa et al., "$C_2$–Symmetric 1,2–Diamine/Copper(ii) Trifluoromethanesulfonate Complexes as Chiral Catalysts. Asymmetric Cyclopropanations of Styrene with Diazo Esters", *Tetrahedron Letters*, vol. 35, No. 43, 1994, pp. 7985–7988.

R.E. Lowenthal et al., "Asymmetric Copper–Catalyzed Cyclopropanation of Trisubstituted and Unsymmetrical cis–Disubstituted Olefins": Modified Bis–Oxazoline Ligands, Tetrahedron Letters, vol. 32, No. 50, 1991, pp. 7373–7376, XP002087674, p. 7374, Table 1.

S. Kanemasa et al., "C2–Symmetric 1.2–Diamine/Copper (II) Trifluoromethanesulfonate Complexes as Chiral Catalysts. Asymmetric Cyclopropanations of Styrene with Diazo Esters," Tetrahedron Letters, vol. 35, No. 43, 1994, pp. 7985–7988, XP002100966, p. 7985, abstract and scheme 2.

Database WPI AN 77–70015Y (Sep. 5, 1997).

HU 188255 B (Mar. 28, 1985) Abstract.

*Primary Examiner*—Paul J. Killos
(74) *Attorney, Agent, or Firm*—Sughrue, Mion, Zinn, Macpeak & Seas, PLLC

(57) ABSTRACT

The present invention provides an advantageous method for producing an optically active chrysanthemic acid. Disclosed is a method for producing an optically active chrysanthemic acid whose trans isomer ratio and optical purity are improved, which comprises reacting chrysanthemic acid having a trans isomer ratio of not less than 50% and an optical purity of not less than 10% e.e. with an optically active organic amine to optically resolve said chrysanthemic acid.

5 Claims, No Drawings

PROCESS FOR PRODUCING OPTICALLY ACTIVE CHRYSANTHEMIC ACID

BACKGROUND OF THE INVENTION

1. Filed of the Invention

The present invention relates to a method for producing an optically active chrysanthemic acid (cyclopropanecarboxylic acid) derivative.

2. Description of the Related Art

Optically active cyclopropanecarboxylic acid derivatives are important intermediates for drugs and pesticides. For example, (+)-2,2-dimethyl-3-(2-methyl-1-propenyl) cyclopropanecarboxylic acid known as chrysanthemum mono-carboxylic acid constitutes an acid component of synthetic pyrethroid insecticide.

The insecticidal activity of a trans-pyrethroid ester is usually higher than that of a cis-isomer. Particularly, pyrethroid esters of (+)-trans-chrysanthemum mono-carboxylic acid(hereinafter referred to as "chrysanthemic acid") or chrysanthemic acid enriched with the (+)-trans-chrysanthemic acid have exhibited excellent insecticidal activity. Accordingly, an industrially advantageous method to produce (+)-trans-chrysanthemic acid or chrysanthemic acid enriched with the (+)-trans-chrysanthemic acid has been desired.

As a method of producing an optically active chrysanthemic acid derivative by using a synthetic technique, there has been known a method of reacting a (±)-trans-chrysanthemum mono-carboxylic acid or trans rich (±)-chrysanthemum mono-carboxylic acid with an optical resolution agent, which are an optically active amine, to obtain an optically active chrysanthemic acid (JP46-20382B/1971, JP54-37130B/1979, JP49-109344A/1974 and JP51-23497B/1976). However, these optical resolution methods were not always satisfactory, because of low yield of the desired optically active chrysanthemic acid.

Therefore, the present inventors have intensively studied. As a result, they have found that, when chrysanthemic acid optically enriched with one isomer, e.g. (+)-trans-chrysanthemic acid can be purified by crystallization using an optical active amine in the production of an optically active chrysanthemic acid, whereby (+)-trans-chrysanthemic acid having excellent optical purity can be obtained with surprisingly good efficiency compared with the case of using racemic chrysanthemic acid, and trans isomer ratio of the chrysanthemic acid can also be improved efficiently when trans isomer having not less than 50% trans-isomer ratio are applied.

SUMMARY OF THE INVENTION

The present invention provides:

1. a method for producing an optically active chrysanthemic acid whose trans isomer ratio and optical purity are improved, which comprises:

reacting chrysanthemic acid having a trans isomer ratio of not less than 50% and an optical purity of not less than 10% e.e. with an optically active organic amine to optically resolve said chrysanthemic acid; and 2. a method for producing an optically active chrysanthemic acid whose trans isomer ratio and optical purity are improved, which comprises:

reacting 2,5-dimethyl-2,4-hexadiene with diazoacetates of the formula (1):

$$N_2CHCO_2R_7 \tag{I}$$

wherein $R_7$ represents an alkyl group having 1 to 6 carbon atoms or a cycloalkyl group, in the presence of an asymmetric copper complex to produce an optically active chrysanthemic add ester (cyclopropanation step), contacting chrysanthemic acid esters with an acid or base to form chrysanthemic acid (hydrolysis step); and optically resolving chrysanthemic acid using at least one optically active organic amine selected from those of the formulas (A-1), (A-2), (A-3) and (A-4) shown below (optical resolution step).

DESCRIPTION OF THE PREFERRED EMBODIMENTS

First, a description will be made to the method for producing an optically active chrysanthemic acid of which trans isomer ratio and optical purity are improved, which comprises:

reacting chrysanthemic acid having a trans isomer ratio of not less than 50% and an optical purity of not less than 10% e.e. with an optically active organic amine to optically resolve said chrysanthemic acid.

Chrysanthemic acid having a trans isomer ratio of not less than 50% and an optical purity of not less than 10% e.e. can be obtained by any method, for example, it can be produced in the following manner.

In the present invention, the "optical purity" or e.e. % of (+)-trans-chrysanthemic acid in the trans isomer is calculated based on the analysis using optically active column and is defined, for example, by the following equation: 100 ×{[(+-trans-chrysanthemic acid–(–)-trans-chrysanthemic acid]/[(+)-trans-chrysanthemic acid+(–)-trans-chrysanthemic acid]}.

The optically active chrysanthemic acid can be obtained by reacting 2,5-dimethyl-2,4-hexadiene with diazoacetate of the formula (I):

wherein $R_7$ represents an alkyl group having 1 to 6 carbon atoms or a cycloalkyl group, in the presence of an asymmetric copper complex to produce optically active chrysanthemic acid esters (cyclopropanation step); and decomposing chrysanthemic acid esters with an alkali or acid (hydrolysis step).

In this method trans isomer ratio of not less than 50% and optical purity of not less than 20% e.e. is preferably employed, more preferably, chrysanthemic acid having trans isomer ratio of from 60% e.e. to 95% e.e. and optical purity of from 30% e.e. to 90% e.e. is employed.

The optically active organic amine for optically resolving the optically active chrysanthemic acid includes, for example, an optically active organic amine of the formula (A-1):

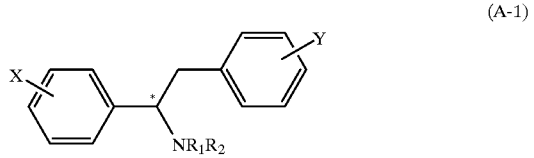

wherein $R_1$ and $R_2$ respectively represent a hydrogen atom, an alkyl group, an aralkyl group or an aryl group;

X and Y respectively represent a hydrogen atom, a halogen atom, a lower alkyl group or a lower alkoxyl group; and

* represents an asymmetric carbon atom; or
an optically active organic amine of the formula (A-2):

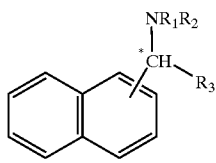

(A-2)

wherein $R_1$ and $R_2$ respectively represent a hydrogen atom, an alkyl group, an aralkyl group or an aryl group;

$R_3$ represents an alkyl group having 1 to 6 carbon atoms, and

* represents an asymmetric carbon atom; or
an optically active organic amine of the formula (A-3):

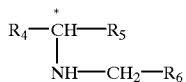

(A-3)

wherein $R_4$ represents a naphthyl group, a cyclohexyl group, or a phenyl group which may be substituted with halogen, nitro, lower alkyl or lower alkoxy;

$R_5$ represents a lower alkyl group, or a benzyl group which may be substituted with a lower alkyl group;

$R_6$ represents a p-hydroxyphenyl group or a 2-hydroxy-3-lower alkoxyphenyl group when $R_5$ is a lower alkyl group, and $R_6$ represents a p-hydroxyphenyl group when $R_5$ is a benzyl group which may be substituted with a lower alkyl group, and

* represents an asymmetric carbon atom, or an optically active organic amine of the formula (A-4):

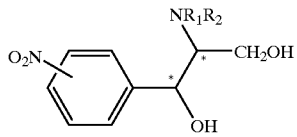

(A-4)

wherein $R_1$ and $R_2$ respectively represent a hydrogen atom, an alkyl group, an aralkyl group or an aryl group, and

* represents an asymmetric carbon atom.

The optically active amine includes, for example, optically active compounds such as 1-phenyl-2-(p-tolyl)ethylamine, α-(1-naphthyl)-ethylamine,
α-(2-naphthyl)-ethylamine, 1-phenylethylamine,
erythro-α,β-diphenyl-β-hydroxyethylamine,
N-methylephedrine,
N-(2,2,2-trichloro-1-formamideethyl)piperidine,
2-benzylamino-1-butanol,
ephedrine, cis-N-benzyl-2-(hydroxymethyl)cyclohexylamine,
N-(p-hydroxybenzyl)-1-phenylethylamine,
N-(p-hydroxybenzyl)-1-(p-tolyl)ethylamine,
N-(p-hydroxybenzyl)-1-(p-isopropylphenyl)ethylamine,
N-(p-hydroxybenzyl)-1-(p-nitrophenyl)ethylamine,
N-(p-hydroxybenzyl)-1-(p-bromophenyl)ethylamine,
N-(p-hydroxybenzyl)-1-(1-naphthyl)ethylamine,
N-(p-hydroxybenzyl)-1-cyclohexylethylamine,
N-(p-hydroxybenzyl)-1-(p-methoxyphenyl)ethylamine,
N-(p-hydroxybenzyl)-1-phenylpropylamine,
N-(p-hydroxybenzyl2-methyl-1-phenylpropylamine,
N-(2-hydroxy-3-methoxybenzyl)-1-phenylethylamine,
N-(2-hydroxy-3-methoxybenzyl)-1-(p-tolyl)ethylamine,
N-(2-hydroxy-3-methoxybenzyl)-1-(p-isopropylphenyl)ethylamine,
N-(2-hydroxy-3-methoxybenzyl)-1-(p-nitrophenyl)ethylamine,
N-(2-hydroxy-3-methoxybenzyl)-1-(p-bromophenyl)ethylamine,
N-(2-hydroxy-3-methoxybenzyl)-1-(1-naphthyl)ethylamine,
N-(2-hydroxy-3-methoxybenzyl)-1-cylohexylethylamine,
N-(2-hydroxy-3-methoxybenzyl)-1-(p-methoxyphenyl)ethylamine,
N-(2-hydroxy-3-methoxybenzyl)-1-phenylpropylamine,
N-(2-hydroxy-3-methoxybenzyl)-2-methyl-1-phenylpropylamine,
N-p-hydroxybenzyl-α-phenyl-β-paratolylethylamine,
erythro-1-p-nitrophenyl-2-N,N-dimethylaminopropane-1,3-diol, and
threo-1-p-nitrophenyl-2-N,N-dimethylaminopropane-1,3-diol.

Optical resolution is performed by reacting the optically active chrysanthemic acid with an optically active amine (optical resolution agent) of the formula (A-1), (A-2), (A-3) or (A-4).

The optical resolution is usually performed in a solvent. As the solvent, there can be used aromatic hydrocarbons such as benzene, toluene and xylene; aliphatic hydrocarbons such as hexane and heptane; alcohols such as water, methanol and ethanol; ketones such as acetone and methyl isobutyl ketone; and ethers such as dioxane and tetrahydrofuran. These solvents may be used alone or in combination thereof.

The amount of the solvent varies depending on the solvent and conditions of the post treatments and is not specifically limited, and an optimum amount is optionally set according to the respective conditions.

The amount of the optical resolution agent is usually from about 0.2 to 1.2 mol, and preferably from about 0.3 to 1.1 mol, per mol of chrysanthemic acid.

The optical resolution agent and chrysanthemic acid are usually dissolved in the solvent above under stirring or standing. The mixture may be heated to dissolve, if necessary.

A diastereomer crystal comprising an optical resolution agent and optically active chrysanthemic acid is usually formed to deposit from the solution on standing at an ambient temperature or by cooling the solution.

The deposited crystal may be collected as it is, or alternatively, it may be totally or partially dissolved by heating and then cooled to deposit the crystal, if necessary.

The dissolution and deposition is usually conducted at a temperature ranging from −20 to 150° C., and preferably from −10 to 100° C.

The deposited diastereomer crystal is usually separated by filtration.

The diastereomer salt separated as a crystal is then decomposed with an acid or alkali and extracted to obtain the optically active chrysanthemic acid with higher trans ratio and optical purity. The used optical resolution agent can be recovered.

For example, an optically active chrysanthemic acid is obtained by decomposing the diastereomer salt, obtained by means of the above method, with hydrochloric acid or sulfuric acid and extracting the resultant with an organic solvent. Furthermore, the agent for optical resolution is recovered by making the aqueous layer weak alkali and extracting it.

Alternatively, the optical resolution agent can be recovered by decomposing the disatereomer salt, obtained by means of the above method, with a base such as sodium hydroxide, and extracting the resultant with an organic solvent in the weak alkali condition. Thereafter, the aqueous layer is acidified and extracted, thereby making it possible to obtain an optically active chrysanthemic acid.

The optical resolution agent recovered by these methods can be reused.

Next a description will be made to the method for producing an optically active chrysanthemic acid, which comprises reacting 2,5-dimethyl-2,4-hexadiene with diazoacetates of the formula (I) as defined above, in the presence of an asymmetric copper complex to produce optically active chrysanthemic acid esters (cyclopropanation step); and contacting the chrysanthemic acid ester with an alkali or acid (hydrolysis step).

The alkyl group of diazoacetate used in the above cyclopropanation step includes, for example, methyl, ethyl, n-propyl, iso-propyl, n-butyl, iso-butyl, t-butyl, pentyl, hexyl and cyclohexyl groups.

The asymmetric copper complex used in the above cyclopropanation step is prepared from a copper compound and an optically active organic compound (hereinafter referred to as "an optically active ligand") (Pure & Appl. Chem., Vol. 57, No. 12, 1839, 1985, Tetrahedron Left., 32, 7373 (1991), Tetrahedron Lett., 35, 7985 (1994)).

The copper compound includes, for example, mono- or divalent copper compounds such as copper naphthenate, copper trifluoromethanesulfonate, copper acetate, copper bromide and copper chloride. These compounds may be used alone or in combination thereof.

The optically active ligand includes, for example, optically active bisoxazoline compound, optically active salicylideneamino alcohol compound, optically active diamine compound, optically active semicorrin compound and optically active camphor compound.

Preferred examples thereof include optically active salicylideneamino alcohol compound, optically active bisoxazoline compound and optically active ethylenediamine compound.

The optically active bisoxazoline compound is of the formula (L-1):

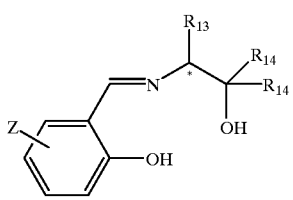

(L-1)

wherein $R_8$ and $R_9$ are different and represent an optionally substituted phenyl group or a hydrogen atom, $R_{10}$ and $R_{11}$ represent a hydrogen atom, an alkyl group, a cycloalkyl group, an optionally substituted phenyl group or an aralkyl group, or $R_{10}$ and $R_{11}$ may be combined to form a cyclic alkylene group; and $R_{12}$ represents a hydrogen atom or an alkyl group.

The optically active bisoxazoline compound (L-1) includes, for example, 2,2'-methylenebis[(4R)phenyl-5,5-dimethyloxazoline], 2,2'-methylenebis[(4R)-phenyl-5,5-diethyloxazoline], 2,2'-methylenebis[(4R)-phenyl-5,5-di-n-propyloxazoline], 2,2'-methylenebis[(4R)-phenyl-5,5-di-i-propyloxazoline], 2,2'-methylenebis[(4R)-phenyl-5,5-dicyclohexyloxazoline], 2,2'-methylenebis[(4R)-phenyl-5,5-diphenyloxazoline], 2,2'-methylenebis[(4R)-phenyl-5,5di-(2-methylphenyl) oxazoline], 2,2'-methylenebis[(4R)-phenyl-5,5-di-(3-methylphenyl)oxazoline], 2,2'-methylenebis[(4R)-phenyl-5,5-di-(4-methylphenyl) oxazoline],
2,2'-methylenebis[(4R)-phenyl-5,5-di-(2-methoxyphenyl) oxazoline],
2,2'-methylenebis[(4R)-phenyl-5,5-di-(3-methoxyphenyl) oxazoline],
2,2'-methylenebis[(4R)-phenyl-5,5di-(4-methoxyphenyl) oxazoline],
2,2'-methylenebis[spiro{(4R)-phenyloxazoline-5,1'-cyclobutane}],
2,2'-methylenebis[spiro{(4R)-phenyloxazoline-5,1'-cyclopentane}],
2,2'-methylenebis[spiro{(4R)-phenyloxazoline-5,1'-cyclohexane}],
2,2'-methylenebis[spiro{(4R)-phenyloxazoline-5,1'-cycloheptane}] and
compounds wherein (4R) in the above respective compounds is replaced by (4S).

The optically active salicylideneamino alcohol compound includes a compound of the formula (L-2):

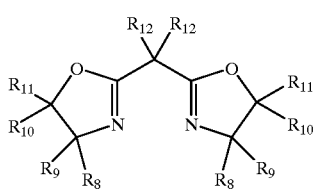

(L-2)

wherein $R_{13}$ and $R_{14}$ respectively represent an alkyl group, an aralkyl group or an aryl group, Z represents a hydrogen atom, a halogen atom, an alkyl group, an alkoxy group, an aralkyl group or an aryl group, and

* represents an asymmetric carbon atom.

$R_{13}$ of the optically active salicylideneamino alcohol compound (L-2) includes, for example, methyl, ethyl, iso-propyl, iso-butyl, t-butyl, benzyl and phenyl groups.

$R_{14}$ includes, for example, methyl, ethyl, iso-propyl, iso-butyl, t-butyl and benzyl groups, and phenyl group which may be substituted with an alkyl group, a it halogen atom or an alkoxy group.

Specific examples of the compound of the formula (L-2) includes (R) isomer or (S) isomer of the following compounds:

N-salicylidene-2-amino-1,1-diphenyl-1-propanol,
N-salicylidene-2-amino-1,1-di(3-methylphenyl)-propanol,
N-salicylidene-2-amino-1,1-di(4-methylphenyl)-1-propanol,
N-salicylidene-2-amino-1,1-di(2-methoxyphenyl)-propanol,
N-salicylidene-2-amino-1,1-di(2-ethoxyphenyl-1-propanol,
N-salicylidene-2-amino1,1-di(2-isopropoxyphenylyl)-1-propanol,
N-salicylidene-2-amino-1,1 di(2-n-butoxy-5-t-butylphenyl)-1-propanol,
N-salicylidene-2-amino-1,1-diphenyl-3-methyl-1-butanol,
N-salicylidene-2-amino-1,1-di(3-methylphenyl)-3-methyl-1-butanol, N-salicylidene-2-amino-1,1-di(4-methylphenyl)phenyl-3-methyl-1-butanol,
N-salicylidene-2-amino1,1-di(2-methoxyphenyl)-3-methyl-1-butanol,
N-salicylidene-2-amino-1,1-dip(2-ethoxthenyl)-3-methyl-1-butanol,
N-salicylidene-2-amino-1,1-di(2-isopropoxyphenyl)-3-methyl-1-propanol,
N-salicylidene-2-amino-1,1-di(2-n-butoxy-5-t-butylphenyl-3-methyl-1-butanol,
N-salicylidene-2-amino-1,1-diphenyl-4-methyl-1-pentanol,
N-salicylidene-2-amino-1,1-di(3-methylphenyl)-methyl-1-pentanol,
N-salicylidene-2-amino-1,1-di(4-methylphenyl)-4-methyl-1-pentanol,
N-salicylidene-2-amino-1,1-di(2-methoxtphenylphenyl)-4-methyl-1-pentanol,
N-salicylidene-2-amino-1,1-di(2-ethoxyphenyl)-4-methyl-1-pentanol,
N-salicylidene-2-amino-1,1-di(2-isopropoxyphenyl)-4-methyl-1-pentanol,
N-salicylidene-2-amino-1,1-di(2-n-butoxy-5-t-butylphenyl)-4-methyl-1-pentanol,
N-salicylidene-2-amino-1,1-diphenyl-3-phenyl-1-propanol,
N-salicylidene-2-amino-1,1-di(3-methylphenyl)-3phenyl-1-propanol,
N-salicylidene-2-amino-1,1-di(4-methylphenyl)-3-phenyl-1-propanol,
N-salicylidene-2-amino1,1-di(2-methoxylphenyl)-3-phenyl-1-propanol,
N-salicylidene-2-amino-1,1-di(2-ethoxylphenyl)-3-phenyl-1-propanol,
N-salicylidene-2-amino-1,1-di(2-isopropoxylphenyl)-3phenyl-1-propanol, and
N-salicylidene-2-amino-1,1-di(2-n-butoxy-5-t-butylphenyl)-3-phenyl-1-propanol.

The optically active ethylenediamine alcohol compound includes a compound of the formula (L-3):

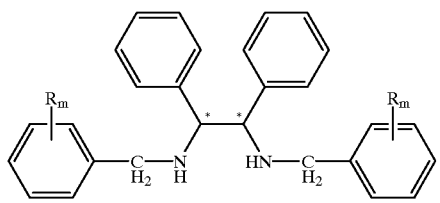

(L-3)

wherein R represents a hydrogen atom or a lower alkyl group,
m represents an integer of 1 to 3, and
*represents an asymmetric carbon atom.

Specific compound of the optically active ethylenediamine compound (L-3) includes, for example, compounds wherein R is a hydrogen atom or a methyl group and m is an integer of 1 to 3.

Specific examples thereof includes bis[N-(2,4,6-trimethylphenyl)methyl-(1R),(2R)-diphenylethylenediamine and an antipode thereof having (1S), (2S) configuration.

The asymmetric copper complex can be prepared by mixing the above copper compound with the optically active ligand in a solvent.

The solvent used herein includes, for example, aromatic hydrocarbons such as toluene and xylene and aliphatic halogenated hydrocarbons such as dichloromethane and dichloroethane. Furthermore, 2,5-dimethyl-2,4-hexadiene may also be used as the solvent.

The solvent is usually used in a 10- to 500-fold amount based on the weight of the copper compound.

The amount of the optically active ligand is usually from about 0.8 to 5 mol, and preferably from about 1 to 2 mol, per mol of the copper compound.

In view of the reaction yield, water is preferably excludes in the above reaction.

The above reaction temperature is not specifically limited. The reaction is usually carried out at the temperature within a range from about 0 to 50° C.

In the present invention, when the complex is prepared by using a divalent copper compound, an object can be sufficiently attained even if the divalent copper compound is not reduced to form a monovalent copper compound by using a reducing agent such as phenylhydrazine.

The reaction between the copper compound and the optically active ligand is usually carried out in the atmosphere of an inert gas such as argon and nitrogen.

The asymmetric copper complex can be obtained in such a manner, but the copper complex may be isolated or can be used as it is in the reaction between 2,5-dimethyl-2,4-hexadiene and the diazoacetate (I) without being isolated.

The amount of the asymmetric copper complex used in the reaction between 2,5-dimethyl-2,4-hexadiene and the diazoacetates (I) is usually from about 0.0001 to 0.01 mol, and preferably from about 0.0005 to 0.01 mol, per mol of the diazoacetate (1).

Specific method of reacting 2,5-dimethyl-2,4-hexadiene with the diazoacetate (I) in the presence of the asymmetric copper complex includes, for example, a method adding the diazoacetate (I) dissolved in a solvent to a mixture of the asymmetric copper complex obtained as described above and 2,5-dimethyl-2,4-hexadiene.

The solvent includes, for example, halogenated hydrocarbons such as dichloromethane, 1,2-dichloroethane, chloroform and carbon tetrachloride; aliphatic hydrocarbons such as hexane, heptane and cyclohexane; aromatic hydrocarbons such as benzene, toluene and xylene; and esters such as methyl acetate and ethyl acetate. It is also possible to use 2,5-dimethyl-2,4-hexadiene as the solvent. These solvents can also be used in combination.

The solvent is usually used in a 1- to 30-fold amount, and preferably 5- to 20-fold amount, based on the weight of the diazoacetate (I).

The reaction between 2,5-dimethyl-2,4-hexadiene and the diazoacetate (l) is usually carried out in an atmosphere of an inert gas such as argon and nitrogen.

2,5-dimethyl-2,4-hexadine is usually used in the amount of 1 to 50 mol, and preferably 5 to 30 mol, per mol of the diazoacetate (I).

In view of the reaction yield, water is preferably excluded in the above reaction.

The above reaction temperature is not specifically limited. The reaction can be carried out at the temperature of not more than a boiling point of the solvent when using the solvent, but is usually carried out at the temperature within a range from about 0 to 120° C., and preferably from 5 to 100° C.

The optically active chrysanthemic acid esters with considerably good purity can be obtained in the above reaction by distilling off the solvent, but can be optionally isolated by a conventional method such as distillation and column chromatography, if necessary.

The ester residue of the optically active chrysanthemic acid esters obtained by the above reaction includes, for example, methyl, ethyl, n-propyl, i-propyl, i-butyl, t-butyl, pentyl, hexyl and cyclohexyl groups.

The resulting optically active chrysanthemic acid esters can be converted into the corresponding chrysanthemic acid by contacting with an acid or an aqueous alkali solution (hydrolysis step). The amount of an alkali compound of the aqueous alkali solution used is usually from 1 to 20 mol, and preferably from 1 to 10 mol, per mol of the chrysanthemic acid esters.

The chrysanthemic acid, particularly having a trans isomer ratio of not less than 50% and an optical purity of not less than 10% e.e. thus obtained may be used in the optical resolution step as it is, or optionally used in combination with chrysanthemic acid enriched with the trans isomer.

Such chrysanthemic acid enriched with the trans isomer can be obtained, for example, by reacting (−)-cis chrysanthemic acid or chrysanthemic acid enriched with a (−)-trans isomer with t-butyl hydroperoxide and aluminum bromide in the presence of a toluene solvent (see JP5-37137B/1993). The trans isomer ratio of the chrysanthemic acid enriched with the trans isomer used is not less than 80%, and preferably not less than 85%.

According to the present invention, there can be produced chrysanthemic acid having more improved trans/cis ratio and more improved optical purity in an industrially advantageous manner. In the above method, when using chrysanthemic acid having a trans isomer ratio of not less than 50% and an optical purity of not less than 10% e.e., there can be obtained an optically active chrysanthemic acid whose trans isomer ratio and optical purity are improved.

EXAMPLES

The following Examples further illustrate the present invention in detail but are not to be construed to limit the scope thereof.

Example 1

To 20 g of chrysanthemic acid having an optical purity of 72% e.e. with respect to trans isomer and 52% e.e. with respect to cis isomer, and a trans/cis ratio of 78/22, 228 g of toluene was added and dissolved with stirring. Then, 20.4 g of (S)-1-phenyl-2-(p-tolyl)ethylamine (optical resolution agent ) was added thereto and dissolved with heating. After cooling to room temperature, the deposited crystal was collected by filtration, washed with toluene and then dissolved in an aqueous 5% sodium hydroxide. After the optical resolution agent was extracted with toluene, the aqueous layer was acidified with aqueous 5% sulfuric acid and extracted with toluene. Then, toluene was distilled off to obtain 14.3 g of chrysanthemic acid having a trans/cis ratio of 81/19 and an optical purity of 98% e.e. with respect to (+)-trans isomer and 98% e.e. with respect to (+)-cis isomer (yield: 71.5%).

Example 2

To 30 g of chrysanthemic acid having an optical purity of 40% e.e. with respect to (+)-trans isomer and 1.3% e.e. with respect to (+)-cis isomer and a trans/cis ratio of 77/23, 210 g of toluene was added and dissolved with stirring. Then, 24.7 g of (S)-1-phenyl-2-(p-tolyl)ethylamine (optical resolution agent) was added to the solution and dissolved with heating. After cooling to room temperature, the deposited crystal was collected by filtration, washed with toluene and then dissolved in an aqueous 5% sodium hydroxide. After the optical resolution agent was extracted with toluene, the aqueous layer was acidified with aqueous 5% sulfuric acid and extracted with toluene. Then, the toluene was distilled off to obtain 15.1 g of chrysanthemic acid having a trans/cis ratio of 85/15 and an optical purity of 96% e.e. with respect to (+)-trans isomer and 95% e.e. with respect to (+)-cis isomer. (yield: 50.3%).

Example 3

18.05 mg (0.05 mmol) of copper trifluoromethanesulfonate, 19.9 mg (0.055 mmol) of bis[2-[4(R)-phenyl-5,5-dimethyl-2-oxazoline]]methane and 5 ml of n-butyl chloride were charged in a 50 ml Schienk's tube wherein the atmosphere is substituted with nitrogen, followed by stirring at room temperature for 10 minutes. After 30.0 g (275 mmol) of 2,5-dimethyl-2,4-hexadiene was further added, 5.70 g (50 mmol) of ethyl diazoacetate was added dropwise at 50° C. over 2 hours. After the completion of the dropwise addition of ethyl diazoacetate, the mixture was further stirred at 50° C. for 1 hour. The amount of chrysanthemic acid ethyl ester formed was determined by gas chromatography. As a result, it was 8.43 g and the yield was 86.0% based on ethyl diazoacetate and, furthermore, the trans/cis ratio was 72/28. After 2,5-dimethyl-2,4-hexadiene (boiling point: 51° C./30 mmHg) was distilled off from the reaction mixture, 1 g of the concentrated solution was taken out. Then, 10 ml of an aqueous 1N sodium hydroxide solution and 5 ml of ethanol were added and alkali hydrolysis was performed by stirring at 100° C. for 1 hour. The resulting chrysanthemic acid was reacted with I-menthol and the formed diastereomer ester was analyzed by gas chromatography. As a result, the optical purity of the (+)-trans isomer was 60% e.e., whereas, the optical purity of the (+)-cis isomer was 27% e.e.

Furthermore, chrysanthemic acid obtained by hydrolyzing the ethyl chrysanthemate with 1N sodium hydroxide was mixed with racemic chrysanthemic acid enriched with trans isomer (trans/cis ratio: 95/5) in a weight ratio of 6:4. 104.5 g of toluene was then added to 10.0 g of the mixed chrysanthemic acid, and the mixture was dissolved with stirring. Then, 7.48 g of (S)-1-phenyl-2-(p-tolyl)ethylamine (optical resolution agent) was added to the solution and dissolved with heating. After cooling to room temperature, the deposited crystal was collected by filtration, washed with toluene and then dissolved in an aqueous 5% sodium hydroxide. After the agent for optical resolution was extracted with toluene, the aqueous layer was acidified with aqueous 5% sulfuric acid and extracted with toluene to obtain 4.19 g of chrysanthemic acid having a trans/cis ratio of 87/13 and an optical purity of 95% e.e. with respect to (+)-trans isomer and 97% e.e. with respect to (+)-cis isomer (yield: t 41.9%).

Example 4

22.6 mg (0.05 mmol) of copper complex prepared from 9.98 mg (0.05 mmol) of copper acetate-mono hydrate and 21.5 mg of (R)-N-salicylidene-2-amino-1,1-di(2-methoxyphenyl)propanol, and 6.0 g (55 mmol) of 2,5dimethyl-2,4-hexadiene were charged in a 50 ml Schlenk's tube wherein the atmosphere is substituted with nitrogen, followed by the addition of 5.4 mg of phenylhydrazine, and 1.14 g (10 mmol) of ethyl diazoacetate was added dropwise at 80° C. over 2 hours. After the completion of the dropwise addition of ethyl diazoacetate, the mixture was further stirred at 25° C. for 1 hour. The amount of chrysanthemic acid ethyl ester formed was determined by gas chromatography. As a result, it was 1.76 g and the yield was 90.0% based on ethyl diazoacetate and, furthermore, the trans/cis ratio was 58/42. After 2,5-dimethyl-2,4-hexadiene (boiling point: 51° C./30 mmHg) was distilled off from the reaction mixture, 1 g of the concentrated solution was taken out. Then, 10 ml of an aqueous 1N sodium hydroxide solution and 5 ml of ethanol were added and alkali hydrolysis was performed by stirring at 100° C. for 1 hour. The resulting chrysanthemic acid was reacted with I-menthol and the formed diastereomer was analyzed by gas chromatography. As a result, the optical purity of the (+)-trans isomer was 63% e.e., whereas, the optical purity of the (+)-cis isomer was 63% e.e.

Furthermore, chrysanthemic acid obtained by hydrolyzing the ethyl chrysanthemate with 1N sodium hydroxide was mixed with racemic chrysanthemic acid enriched with trans isomer (trans/cis ratio: 95/5) in a weight ratio of 4:6. 106.2 g of toluene was then added to 10.0 g of chrysanthemic acid, and the mixture was dissolved with stirring. Then, 7.40 g of (S)-1-phenyl-2-(p-tolyl)ethylamine (optical resolution agent) was added to the solution and dissolved with heating. After cooling to room temperature, the deposited crystal was collected by filtration, washed with toluene and then dissolved in an aqueous 5% sodium hydroxide. After the optical resolution agent was extracted with toluene, the aqueous layer was acidified with aqueous 5% sulfuric acid and extracted with toluene to obtain chrysanthemic acid having a trans/cis ratio of 81/19 and an optical purity of 99% e.e. with respect to (+)-trans isomer and 96% e.e. with respect to (+)-cis isomer(yield: 40.2%).

Example 5

19.64 mg (0.05 mmol) of a copper complex prepared from 9.98 mg (0.05 mmol) of copper acetate monohydrate and 18.23 mg (0.055 mmol) of (R)-N-salicylidene-2-amino-1,1-diphenylpropanol, and 6.09 (55 mmol) of 2,5-dimethyl-2,4-hexadiene were charged in a 50 ml Schlenk's tube wherein the atmosphere is substituted with nitrogen. After 5.4 mg of phenylhydrazine was further added, 1.14 g (10 mmol) of ethyl diazoacetate was added dropwise at 50° C. over 2 hours. After the completion of the dropwise addition of ethyl diazoacetate, the mixture was further stirred at 25° C. for 1 hour. The amount of chrysanthemic acid ethyl ester formed was determined by gas chromatography. As a result, it was 1.52 g and the yield was 77.7% based on ethyl diazoacetate and, furthermore, the trans/cis ratio was 61/39. After 2,5dimethyl-2,4-hexadiene (boiling point: 51° C./30 mmHg) was distilled off from the reaction mixture, 1 g of the concentrated solution was taken out. Then, 10 ml of an aqueous 1N sodium hydroxide solution and 5 ml of ethanol were added and alkali hydrolysis was performed by stirring at 100° C. for 1 hour. The resulting chrysanthemic acid was reacted with l-menthol and the formed diastereomer ester was analyzed by gas chromatography. As a result, the optical purity of the (+)-trans isomer was 69% e.e., whereas, the optical purity of the (+)-cis isomer was 68% e.e.

Furthermore, chrysanthemic acid obtained by alkali hydrolysis is mixed with racemic chrysanthemic acid enriched with trans isomer (trans/cis ratio: 95/5) in a weight ratio of 46:54. Toluene is then added in an about 10-fold amount based on chrysanthemic acid, and the mixture is dissolved with stirring. Then, (S)-1-phenyl-2-(p-tolyl) ethylamine (optical resolution agent) was added in the amount of about 0.69 mol per mol of chrysanthemic acid and dissolved with heating. After cooling to room temperature, the deposited crystal is collected by filtration, washed with toluene and then dissolved in an aqueous 5% sodium hydroxide. After the agent for optical resolution is extracted with toluene, the aqueous layer is acidified with aqueous 5% sulfuric acid and extracted with toluene to obtain chrysanthemic acid having a trans/cis ratio of about 78/22 and an optical purity of about 95% e.e. with respect to (+)-trans isomer and 99% e.e. with respect to that (+)-cis isomer (yield: about 46%).

Example 6

According to the same manner as that described in Example 5 except for using 32.47 mg (0.05 mmol) of a copper complex prepared from 9.98 mg (0.05 mmol) of copper acetate monohydrate and 32.33 mg (0.055 mmol) of (R)-N-salicylidene-2-amino-1,1-di(2-n-butoxy-5t-butylphenyl)propanol in a 50 ml Schlenk's tube wherein the atmosphere is substituted with nitrogen, the reaction was performed. The amount of chrysanthemic acid ethyl ester formed was determined by gas chromatography. As a result, it was 1.64 g and the yield was 83.7% based on ethyl diazoacetate and, furthermore, the trans/cis ratio was 57/43. After 2,5-dimethyl-2,4-hexadiene (boiling point: 51° C./30 mmHg) was distilled off from the reaction mixture, 1 g of the concentrated solution was taken out. Then, 10 ml of an aqueous 1N sodium hydroxide solution and 5 ml of ethanol were added and alkali hydrolysis was performed by stirring at 100° C. for 1 hour. The resulting chrysanthemic acid was reacted with 1-menthol and the formed diastereomer was analyzed by gas chromatography. As a result, the optical purity of the (+)-trans isomer was 86% e.e., whereas, the optical purity of the (+)-cis isomer was 84% e.e.

Furthermore, chrysanthemic acid obtained by alkali hydrolysis is mixed with racemic chrysanthemic acid enriched with trans isomer (trans/cis ratio: 95/5) in a weight ratio of 51:49. Toluene is then added in an about 10-fold amount based on chrysanthemic acid, and the mixture is dissolved with stirring. Then, (S)-1-phenyl-2-(p-tolyl) ethylamine (optical resolution agent) is added in the amount of about 0.68 mol per mol of chrysanthemic acid and dissolved with heating. After cooling to room temperature, the deposited crystal is collected by filtration, washed with toluene and then dissolved in an aqueous 5% sodium hydroxide. After the agent for optical resolution is extracted with toluene, the aqueous layer is acidified with aqueous 5% sulfuric acid and extracted with toluene to obtain chrysanthemic acid having a trans/cis ratio of about 72/28 and an optical purity of the (+)-trans isomer is about 95% e.e. and that of (+)-cis isomer is about 99% e.e. (yield: about 51%).

Comparative Example 1

To 100 g of a racemic chrysanthemic acid (trans/cis ratio: 75/25), 390 g of toluene was added, and the mixture was dissolved with stirring. Then, 47.0 g of (S)-1-phenyl-2-(p-tolyl)ethylamine (optical resolution agent) was added and dissolved with heating. After cooling to room temperature, the deposited crystal was collected by filtration, washed with toluene and then dissolved in an aqueous 5% sodium hydroxide. After the agent for optical resolution was extracted with toluene, the aqueous layer was acidified with aqueous 5% sulfuric acid and extracted with toluene to obtain 20.8 g of chrysanthemic acid having a trans/cis ratio of 80/20 and an optical purity of the (+)-trans isomer was 96% e.e. and that of (+)-cis isomer was 98% e.e.(yield: 20.8%).

Example 7

18.05 mg (0.05 mmol) of trifluoromethanesulfonic acid, 19.9mg(0.055 mmol), bis[2-[4-(R)-phenyl-5,5-dimethyl-2-oxazoline]]methane and 5 ml of n-butyl chloride were charged in a nitrogen charged 50 ml Schlenk's tube, and stirred for 10 min at room temperature. After 6.0 g (55 mmol) of 2,5-dimethyl-2,4-hexadiene were added thereto, 1.41 g (10 mmol) of t-butyl diazoacetate was added dropwise at 25° C. over 1 hour. The amount of chrysanthemic acid t-butyl ester formed was determined by gas chromatography. As a result, it was 1.86 g and the yield was 83.1% based on t-butyl diazoacetate and, furthermore, the trans/cis ratio was 85/15. After 2,5dimethyl-2,4-hexadiene (boiling point: 51° C./30 mmHg) was distilled off from the reaction mixture, the concentrated solution was subjected to luquid chromatography to measure the otpical activity, which revealed the optical purity of (+)-trans isomer was 86% e.e. and that of (+)-cis isomer was 67% e.e.

Then, trans-rich racemic chrysanthemic obtained by decomposing the t-butyl chrysanthemate with trifluoroacetic acid is mixed with racemic chrysanthemic acid of which trans/cis ratio is 95/5 in a weight ratio of 60:40, and 10-fold amount of toluene to the chrysanthemic acid is added to the mixture, stirred and dissolved. Then, 1.0 mole of (S)-α-(1-naphthyl)-ethylamine, as a resolution agent, and 8% by weight of water per chrysanthemic acid are added thereto and the resulting mixture is heated to dissolved. After cooling the mixture to room temperature, deposited crystals are collected by filtration, washed with toluene, then dissolved in aqueous 5% sodium hydroxide and extracted with toluene. Separated water layer is acidified with aqueous 5% sulfuric acid and extracted with toluene to give chrysanthemic acid with a trans/cis ratio of about 98/2 and optical purity of the (+)-trans isomer is about 96% e.e. and that of (+)-cis isomer is about 57% e.e. in a yield of about 57%.

Example 8

19.64 mg (0.05 mmol) of copper complex prepared from 9.98 mg (0.05 mmol) of copper acetate monohydrate, and 18.23 mg of (R)-N-salicylidene-2-amino-1,1-diphenylpropanol, and 6.0 g(55 mmol) of 2,5dimethyl-2,4-hexadiene were charged in a 50 ml Schienk's tube wherein the atmosphere was replaced with nitrogen, and then 5.4 mg of phenylhydrazine. 1.14 g (10 mmol) of ethyl diazoacetate was added dropwise at 50° C. over 2 hours and further stirred for 1 hour at 25° C. The amount of chrysanthemic acidethyl ester formed was determined by gas chromatography. As a result, it was 1.52 g and the yield was 77.7% based on t-butyl diazoacetate and, furthermore, the trans/cis ratio was 61/39. After 2,5-dimethyl-2,4-hexadiene (boiling point: 51° C./30 mmHg) was distilled off from the reaction mixture. Then, 10 ml of an aqueous 1N sodium hydroxide solution and 5 ml of ethanol were added to 1 g of the concentrate and alkali hydrolysis was performed by stirring at 100° C. for 1 hour. The obtained chrysanthemic acid was reacted with I-menthol, and the resulted diastereomer was analyzed by gas chromatography, which showed the optical purity of (+)-trans isomer was 69% e.e. and that of (+)-cis isomer was 68% e.e.

Then, the chrysanthemic acid obtained by the alkali hydrolysis is mixed with trans-rich racemic chrysanthemic acid of which trans/cis ratio is 95/5 is mixed with the (+)-trans isomer in a weight ratio of 43:57, and 7-fold amount of toluene to the chrysanthemic acid is added to the mixture, stirred and dissolved. Then, 1.0 mole of (S)-α-(1-naphthyl)ethylamine, as a resolution agent, and 8% by weight of water to chrysanthemic acid are added thereto and the resulting mixture is heated to dissolved. After cooling the mixture to room temperature, deposited crystals are collected by filtration, washed with toluene, then dissolved in aqueous 5% sodium hydroxide and extracted with toluene. Separated water layer is acidified with aqueous 5% sulfuric acid and extracted with toluene to give chrysanthemic acid with a trans/cis ratio of about 98/2 and optical purity of about 96% e.e. with respect to (+)-trans isomer in a yield of about 40%.

Comparative Example 2

To 16.3 g of a racemic chrysanthemic add (trans/cis ratio: 79/21), 65.0g of toluene was added, and the mixture was dissolved with stirring. Then, 16.0 g of (S)-α-(1-naphthyl) ethylamine (optical resolution agent) and 1.3 g of water were added and dissolved with heating. After cooling to room temperature, the deposited crystal was collected by filtration, washed with toluene and then dissolved in an aqueous 5% sodium hydroxide. After the agent for optical resolution was extracted with toluene, the aqueous layer was acidified with aqueous 5% sulfuric acid and extracted with toluene to obtain 4.13 g of chrysanthemic acid having a trans/cis ratio of 98/2 and an optical purity of 97% e.e. with respect to (+)-trans isomer and 73% e.e. with respect to (+)-cis isomer (yield: 25.3%).

What is claimed is:

1. A method for producing an optically active chrysanthemic acid having improved trans isomer ratio and optical purity, comprising the step of reacting chrysanthemic acid having a trans isomer ratio of not less than 50% and an optical purity of not less than 10% e.e. with an optically active amine to optically resolve said chrysanthemic acid, wherein said optically active amine is an optically active amine of formula (A-1)

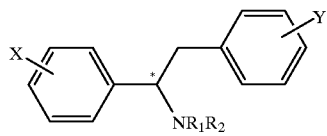

(A-1)

wherein $R_1$ and $R_2$ respectively represent a hydrogen atom, an alkyl group, an aralkyl group or an aryl group, X and Y respectively represent a hydrogen atom, a halogen atom, a lower alkyl group or a lower alkoxyl group, and

* represents an asymmetric carbon atom; or an optically active amine of formula (A-2):

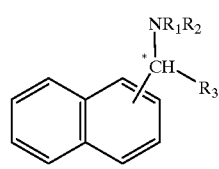

(A-2)

wherein $R_1$ and $R_2$ respectively represent a hydrogen atom, an alkyl group, an aralkyl group or an aryl group, $R_3$ represents an alkyl group having 1 to 6 carbon atoms, and

* represents an asymmetric carbon atom; or an optically active organic amine of formula (A-3):

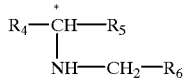
(A-3)

wherein $R_4$ represents a naphthyl group, a cyclohexyl group, or a phenyl group which may be substituted with halogen, nitro, lower alkyl or lower alkoxy, $R_5$ represents a lower alkyl group, or a benzyl group which may be substituted with a lower alkyl group, $R_6$ represents a p-hydroxyphenyl group or a 2-hydroxy-3-lower alkoxyphenyl group when $R_5$ is a lower alkyl group, and $R_6$ represents a p-hydroxyphenyl group when $R_5$ is a benzyl group which may be substituted with a lower alkyl group, and

* represents an asymmetric carbon atom; or an optically active organic amine of formula (A-4):

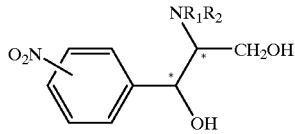
(A-4)

wherein $R_1$ and $R_2$ respectively represent a hydrogen atom, an alkyl group, an aralkyl group or an aryl group, and

* represents an asymmetric carbon atom.

2. The method according to claim 1, wherein a chrysanthemic acid having a trans isomer ratio of 60–95% and an optical purity of 30–90% e.e. is reacted with said optically active amine.

3. A method for producing an optically active chrysanthemic acid, comprising the steps of reacting 2,5-dimethyl-2,4-hexadiene with diazoacetates of the formula (I):

(I)

wherein $R_7$ represents an alkyl group having 1 to 6 carbon atoms or a cycloalkyl group, in the presence of an asymmetric copper complex in a cyclopropanation step to produce optically active chrysanthemic acid esters;

contacting the chrysanthemic acid esters with an acid or base in a hydrolysis step to form chrysanthemic acid; and optically resolving chrysanthemic acid in an optical resolution step using at least one optically active organic amine of formulas (A-1), (A-2), (A-3) and (A-4):

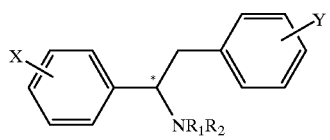
(A-1)

wherein $R_1$ and $R_2$ respectively represent a hydrogen atom, an alkyl group, an aralkyl group or an aryl group, X and Y respectively represent a hydrogen atom, a halogen atom, a lower alkyl group or a lower alkoxyl group, and

* represents an asymmetric carbon atom:

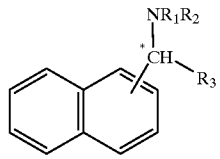
(A-2)

wherein $R_1$ and $R_2$ respectively represent a hydrogen atom, an alkyl group, an aralkyl group or an aryl group, $R_3$ represents an alkyl group having 1 to 6 carbon atoms, and

* represents an asymmetric carbon atom;

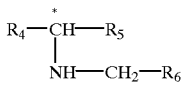
(A-3)

wherein $R_4$ represents a naphthyl group, a cyclohexyl group, or a phenyl group which may be substituted with halogen, nitro, lower alkyl or lower alkoxy, $R_5$ represents a lower alkyl group, or a benzyl group which may be substituted with a lower alkyl group, $R_6$ represents a p-hydroxyphenyl group or a 2-hydroxy-3-lower alkoxyphenyl group when $R_5$ is a lower alkyl group, and $R_6$ represents a p-hydroxyphenyl group when $R_5$ is a benzyl group which may be substituted with a lower alkyl group, and

* represents an asymmetric carbon atom

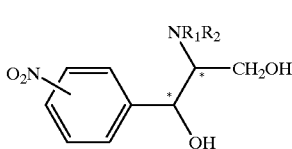
(A-4)

wherein $R_1$ and $R_2$ respectively represent a hydrogen atom, an alkyl group, an aralkyl group or an aryl group, and

* represents an asymmetric carbon atom;

and wherein said asymmetric copper complex is prepared from a copper compound and an optically active ligand selected from the group consisting of an optically active bisoxazoline compound of formula (L-1), an optically active salicylideneamino alcohol compound of formula (L-2) and an optically active ethylenediamine compound of formula (L-3):

(L-1)

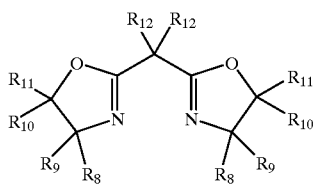

wherein $R_8$ and $R_9$ are different and represent an optionally substituted phenol group or a hydrogen atom, $R_{10}$ and $R_{11}$ represent a hydrogen atom, an alkyl group, a cycloalkyl group, an optionally substituted phenyl group or an aralkyl group, or $R_{10}$ and $R_{11}$ may be combined to form a cyclic alkylene group, and $R_{12}$ represents a hydrogen atom or an alkyl group;

(L-2)

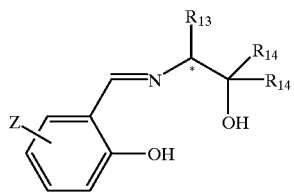

wherein $R_{13}$ and $R_{14}$ respectively represent an alkyl group, an aryl group or an aryl group, Z represents a hydrogen atom, a halogen atom, an alkyl group, an alkoxy group, and aralkyl group or an aryl group, and

* represents an asymmetric carbon atom;

(L-3)

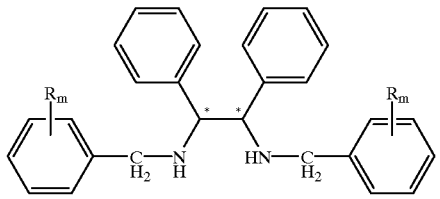

wherein R represents a hydrogen atom or a lower alkyl group, m represents an integer of 1 to 3, and

* represents an asymmetric carbon atom.

4. The method according to claim 1, wherein a chrysanthemic acid having optical purity of not less than 20% e.e. is reacted with an optically active amine.

5. The method according to claim 3, wherein optically active chrysanthemic acid ester in said cyclopropanation step has optical purity of not less than 10% e.e.

* * * * *